United States Patent [19]
Minkkinen et al.

[11] Patent Number: 5,536,887
[45] Date of Patent: Jul. 16, 1996

[54] PROCESS COMPRISING TWO EXTRACTIVE DISTILLATION STEPS FOR THE PRODUCTION OF TERTIARY ETHERS FROM A $C_4$ OR $C_5$ FEEDSTOCK

[75] Inventors: Ari Minkkinen, St Nom la Breteche; Paul Mikitenko, Noisy le Roy; Lionel Asselineau, Paris, all of France

[73] Assignee: Institut Fracnais du Petrole, Rueil Malmaison, France

[21] Appl. No.: 319,691

[22] Filed: Oct. 7, 1994

[30] Foreign Application Priority Data

Oct. 8, 1993 [FR] France ................... 93 12103

[51] Int. Cl.⁶ ............................... C07C 41/00
[52] U.S. Cl. ............................................. 568/697
[58] Field of Search ............................... 568/697

[56] References Cited

U.S. PATENT DOCUMENTS

| | | | |
|---|---|---|---|
| 5,047,070 | 9/1991 | Harandi | 44/446 |
| 5,108,719 | 4/1992 | Harandi | 422/187 |

FOREIGN PATENT DOCUMENTS

| | | |
|---|---|---|
| 2520356 | 7/1983 | France . |
| 2527201 | 11/1983 | France . |
| 2527202 | 11/1983 | France . |
| 2614297 | 10/1988 | France . |
| 2068408 | 8/1981 | United Kingdom . |

OTHER PUBLICATIONS

Marceglia et al., "Snamprogetti's Associated Technologies: Skeletal isomerization of linear olefins; Isobutene via MTBE cracking Butene–1; production Etherification of alternative raw materials" *Chemical Economy and Engineering Review*, vol. 14, No. 6 (No. 159), pp. 35–40, Jun. 1982.

*Primary Examiner*—Paul J. Killos
*Attorney, Agent, or Firm*—Millen, White, Zelano & Branigan

[57] ABSTRACT

Process for the production of tertiary ethers (MTBE, ETBE, TAME, ETAE) in which a hydrocarbon cut (1) containing four or five carbon atoms is reacted with methanol or ethanol (2, 3) in a reactor and recovering ethers (11) and a distillate (10) after distillation ($C_I$). The distillate undergoes a first extractive distillation step in column ($C_{11}$) in the presence of a solvent (27) which is selective towards olefinic hydrocarbons. A saturated hydrocarbon-rich overhead fraction (15) is recovered along with a bottom fraction (18) which is rich in olefins, solvent and alcohol. The olefins (20) are separated from the solvent and alcohol (24) in a second extractive distillation step ($C_{III}$). The olefins are isomerised in a skeletal isomerisation reactor (5) and the isomerate is recycled (2) to reactor (6). The alcohol and solvent are separated in a stripping column ($C_{IV}$). Alcohol (26) is recycled to the synthesis reactor (6) while the solvent (27) is recycled to $C_{II}$. The temperature at the bottom of the second column ($C_{III}$) can be reduced by addition of fresh (4) or recycled (34) alcohol.

21 Claims, 1 Drawing Sheet

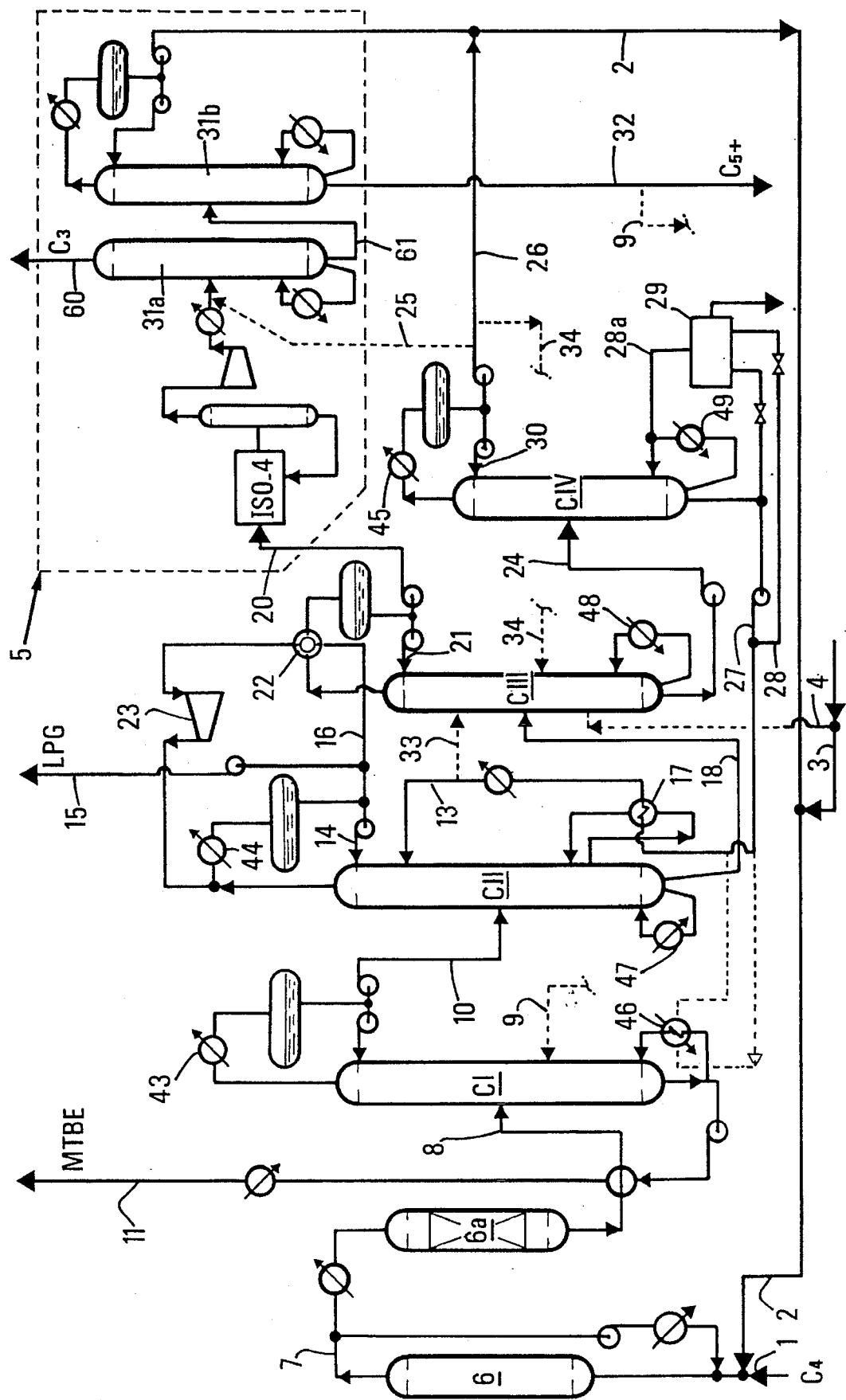

PROCESS COMPRISING TWO EXTRACTIVE DISTILLATION STEPS FOR THE PRODUCTION OF TERTIARY ETHERS FROM A $C_4$ OR $C_5$ FEEDSTOCK

BACKGROUND OF THE INVENTION

The invention concerns a process for the production of tertiary ethers (methyltertiobutylether: MTBE, ethyltertiobutylether: ETBE, methyltertioamylether: TAME, and ethyltertioamylether: ETAE) from a hydrocarbon cut comprising hydrocarbons containing four or five carbon atoms, some of them olefins.

These ethers are introduced into petrols (gasoline) to increase the octane number. The current world demand for MTBE, for example, is increasing at a rate of 25% per annum. This demand cannot be met using iso-olefins containing a tertiary carbon atom which are readily available from existing olefin production units and fluidised bed catalytic crackers. All available olefins must be considered for isomerisation to tertiary olefins, the reactive form, and thus satisfy the future demand for tertiary ethers.

The development of skeletal isomerisation technology now means that this objective can be reached. The combination of the synthesis of tertiary ethers by the reaction of tertiary iso-olefins with methanol or ethanol, and skeletal isomerisation of olefins which do not or only slightly etherify, thus merits all the attention of industrial developers.

The prior art is illustrated in the following patent documents: FR-A-2 527 202, FR-A-2 614 297, FR-A-2 527 201, FR-A-2 520 356, GB-A-2 068 408, and in the publication Chemical Economy and Engineering Review, vol. 14, No. 6, June 1982, pp 35–40 (Integrated isomerisation/MTBE production block flow diagram).

Skeletal isomerisation technology is known not to be without physical and thermodynamic constraints. Only 30% to 50% conversion is possible, with a selectivity of 75% to 85%, necessitating substantial recycling in order to convert all the olefins into tertiary isoolefins. In addition, in order to achieve the performance mentioned, the process must be carried out at rather low pressures, necessitating the use of large equipment to handle the effluent volumes which, in turn, must be compressed for product separation and recovery.

A further obstacle to the efficient combination of skeletal isomerisation and tertiary ether synthesis results from the fact that only the olefin fraction is converted during skeletal isomerisation. Saturated hydrocarbons pass through the isomerisation reactor as if they were inert compounds and are recovered with the isoolefin compounds produced, permanently diluting the reactive hydrocarbons.

The composition of $C_4$ or $C_5$ hydrocarbon cuts from olefin production units and catalytic crackers are very variable due both to their iso-olefin content and to the nature of the olefins present. Effluents from tertiary ether synthesis are thus very different and downstream refining arrangements must be altered as a consequences. Effluents from olefin production units, for example, are rich in linear olefins and poor in saturated hydrocarbons, and are therefore considered to be good isomerisation feedstocks. On the other hand, $C_4$ and $C_5$ effluents from catalytic cracking generally contain more than 50% of saturated hydrocarbons and require downstream equipment which is very bulky which also consumes enormous amounts of energy.

In addition, whatever the quality of the effluents, the skeletal isomerisation product cannot be recycled upstream of the tertiary ether synthesis reactor without a substantial purge of the accumulated saturated hydrocarbons, particularly in the case of feedstocks from catalytic cracking. This purge step thus becomes a major obstacle to the synthesis process. One of the objects of the invention is to overcome the problems or limitations described above, in particular to eliminate at least a portion of the saturated hydrocarbons present in the feedstock before the isomerisation step.

SUMMARY OF THE INVENTION

We have discovered that placing an extractive distillation step for extracting the olefins with a solvent which is selective for olefins between the tertiary ether synthesis step and the unconverted olefin skeletal isomerisation step produces very good results.

In more detail, the invention concerns a process for the production of tertiary ethers comprising the following steps:

a) reacting a hydrocarbon feedstock containing saturated hydrocarbons and tertiary iso-olefinic hydrocarbons, in particular isobutene or 2-methyl 2-butene and 2-methyl 1-butene, with an alcohol which is methanol if the product is methyltertiobutylether (MTBE) or methyltertioamylether (TAME) or ethanol if the product is ethyltertiobutylether (ETBE) or ethyltertioamylether (ETAE) under appropriate synthesis conditions in at least one catalytic reaction zone to produce an effluent containing the tertiary ether, b) distilling the effluent in a distillation zone ($C_I$) under suitable distillation conditions, the tertiary ether being recovered from the bottom of the distillation zone, and a distillate, containing the olefin hydrocarbons, at least a portion of said alcohol and saturated hydrocarbons which may be at least partially condensed, being recovered overhead, c) carrying out extractive distillation of the distillate from step b) in a first extractive distillation zone ($C_{II}$) under appropriate first extractive distillation conditions, in the presence of a non aqueous solvent which is selective for olefin hydrocarbons, at least a portion of which is introduced into said first zone, an overhead fraction being recovered which is rich in at least a portion of the saturated hydrocarbons and which is at least partially condensed, a bottom fraction also being recovered from the first extractive distillation step, d) carrying out extractive distillation of the bottom fraction from step c) in a second extractive distillation zone ($C_{III}$), under suitable second extractive distillation conditions, and recovering overhead at least a portion of a second extractive distillation distillate which is rich in olefin hydrocarbons and which is at least partially condensed, a residue containing mainly alcohol and solvent being recovered from the bottom, e) separating the residue from step d) in a separation zone ($C_{IV}$), under appropriate separation conditions, recovering from the top at least a portion of the alcohol and recycling it at least in part to step a), and recovering solvent from the bottom and recycling it at least in part to step c), and f) carrying out skeletal isomerisation of the distillate from step d) in a skeletal isomerisation zone under appropriate skeletal isomerisation conditions, the zone comprising at least one separation zone for the isomerisation effluents, recovering from said acid separation zone a first isomerisation distillate containing light hydrocarbons and a second isomerisation distillate containing tertiary iso-olefin hydrocarbons which is recycled to step a).

With a $C_4$ feedstock, the separation zone for the isomerisation effluents generally comprises a depropanizer and a debutanizer.

For a $C_5$ feedstock, it generally comprises a debutanizer and a depentanizer.

When producing MTBE or TAME, the alcohol used in all the steps of the process is methanol. Similarly, when producing ETBE or ETAE, the alcohol used is ethanol.

The solvent used is a solvent with substantial selectivity towards olefins. It can be separated from the alcohols by stripping or distillation, it can be separated from the feedstock constituents and it is generally miscible with the feedstock constituents.

Some solvents which fall within these definitions are N,N-dimethylformamide, N,N-diethylformamide, N,N-dimethylacetamide, formylmorpholine, N-methylpyrrolidone, butyrolactone and furfural. All these solvents produce good results, in particular N,N-dimethylformamide.

Advantageously, the second extractive distillation zone is operated at a bottom temperature generally not exceeding 220° C., selected as a function of the solvent to prevent its decomposition.

Advantages of the process over those of the prior art are as follows:

The excess alcohol can be recovered which distils azeotropically with the crude effluent at the top of the hydrocarbon/ether separation column, In addition, recovery of the alcohol from the effluent eliminates the water washing step for the alcohol and the recovery step by stripping used in the prior art. In addition, when using ethanol for the production of ETBE or ETAE, water-free ethanol is obtained following recycling to the ether synthesis reactor. It is known that water-free ethanol cannot be obtained by distillation of the wash water from ethanol water wash operations because of azeotropic limitations. The presence of water in the reactor produces undesirable by-products such as tertiary butyl alcohol.

Economies are thus made as regards both equipment and utilities (reduced use of demineralised water).

When using a preferred solvent such as dimethylformamide, the alcohol extracted acts as a solvent, decreasing the boiling point of the mixture, allowing the olefin fraction to be distilled at a pressure equal to the vapour tension of the olefin fraction and at a temperature which is equal to or substantially below room temperature, without exceeding the temperature of degradation of the solvent. To this end, the content of alcohol as co-solvent can be adjusted so that it is, for example, within the range of 0.1% to 50% by weight, preferably 0.2% to 5% by weight, at the bottom of the column.

In accordance with one feature of the invention, the temperature at the bottom of the second extractive distillation column $C_{III}$ is reduced and controlled by introducing fresh alcohol at a level below that where the bottom fraction from the first extractive distillation column is introduced, for example at a plate which is located in the final third of the column or even into the boiler. The alcohol can be introduced at a ratio of alcohol to bottom fraction of between 0.001 and 1.0.

In accordance with a further feature of the process, a portion of the alcohol from the separation step, for example a stripping step, is recycled to the second extractive distillation column $C_{III}$ at substantially the same level as that described above or to the boiler to obtain a ratio of alcohol to bottom fraction of between 0.001 and 1.0.

In accordance with a still further feature, fresh alcohol and alcohol from the separation step are introduced under the same conditions.

In yet another feature of the process, the remaining portion of solvent which is not introduced into column $C_{II}$ is recycled to the second extractive distillation zone $C_{III}$. This solvent can be introduced at a higher plate than that of the supply to column $C_{III}$ for the bottom fraction from column $C_{II}$. This recycling step minimises the amount of alcohol in the distillate from column $C_{III}$.

According to a still further feature of the process, when using a hydrocarbon mixture from a $C_4$ cut, a portion of the cooled and condensed top fraction from the first extractive distillation column $C_{II}$ containing saturated hydrocarbons is used to cool the distillate leaving the second extractive distillation column $C_{III}$. This top fraction can be vaporised in the grille of a suitable chiller. It is then condensed and reintroduced as reflux into column $C_{II}$. The cooled distillate in the exchanger is then condensed and a portion of this condensed distillate is reintroduced as reflux into column $C_{III}$, while the remaining portion is supplied to the skeletal isomerisation reactor.

The operating conditions in the MTBE, ETBE, TAME or ETAE synthesis reactor and in the distillation column $C_I$ are known to the skilled person. They are described, for example, in patent documents FR-A-2 440 931 and U.S. Pat. No. 4,267,393.

This is also the case for the skeletal isomerisation reactor whose operating conditions are described in United States patent documents U.S. Pat. No. 3,584,070 and U.S. Pat. No. 3,696,163 also in French patent application FR-A-2 695 636.

The structural and operating parameters for the first extractive distillation column $C_{II}$ are generally as follows:

Total efficiency (in theoretical plates): more than 20, preferably 40 to 50;

Pressure: 1 to 25 bar, preferably 4 to 15 bar for a $C_4$ cut and 2 to 12 bar for a $C_5$ cut;

Solvent to feedstock ratio: 3 to 10, preferably 4 to 6;

Reflux rate: more than 0.1, for example 0.15 to 15, preferably 1 to 6.

The conditions in the second extractive distillation zone $C_{III}$ are generally as follows:

Total efficiency (in theoretical plates): more than 10, preferably 25 to 35;

Pressure: 1 to 15 bar, preferably 1,5 to 5 bar;

Solvent to feedstock ratio: 0.01 to 0.5, preferably 0.02 to 0.1;

Reflux rate: more than 0.1, for example 0.1 to 15, preferably 0.2 to 1.

The conditions in the separation column $C_{IV}$ depend on the nature of the extractive distillation solvent and are generally as follows:

Total efficiency (in theoretical plates): more than 5, preferably 10 to 35;

Pressure: 0.1 to 3 bar, preferably 0.6 to 1 bar;

Reflux rate: more than 0.2, preferably 1.5 to 3.5.

Conventional distillation columns or packed columns which are known to the skilled person can be used.

BRIEF DESCRIPTION OF THE DRAWING

The process of the invention is illustrated in the attached figure which is a schematic diagram of MTBE synthesis from isobutene from a $C_4$ catalytic cracking cut and methanol, by way of example. ETBE can, of course, be synthesized using the same scheme, starting from isobutene and ethanol.

DETAILED DESCRIPTION OF THE DRAWING

A mixture of hydrocarbons from a $C_4$ cut is introduced via line 1 into catalytic MTBE synthesis reactor 6 to which line 2 is connected which supplies recycled methanol and $C_4$ olefins from isomerisation unit 5, also line 3 which supplies reactor 6 with fresh methanol. This reactor contains acid resin spheres (for example Amberlyst 15 from ROHM & HAAS as an expanded bed). The exothermic synthesis reaction produces at least about 75% ether. Under these conditions, primary reactor 6 can be followed by secondary reactor 6a which receives effluent from reactor 6 via line 7 and which generally operates at a lower temperature. The isobutene conversion ratio can thus reach 97% but this level of conversion is not absolutely necessary within the context of the present invention. It is desirable to carry out the reaction using an excess of methanol to improve the reaction kinetics. This excess of methanol is generally equivalent to the azeotropic quantity of methanol left in the effluent from the synthesis reaction containing hydrocarbons from the $C_4$ cut which is then recycled to synthesis reactor 6 after separation of the saturated hydrocarbons.

The reaction effluent 8 leaving secondary reactor 6a and containing MTBE, unconverted isobutene, the excess unconverted methanol, other by-products and $C_4$ hydrocarbons which have not reacted, are introduced into conventional or catalytic distillation column $C_I$ at a level which is generally located close to the centre of the column. A distillate is recovered overhead via line 10 which contains constituents with a boiling point which is lower than that of MTBE and a residue is recovered via line 11 which mainly consists of high purity MTBE which can be mixed with petrol or stored. The methanol, in the form of an azeotrope which is formed with the $C_4$ hydrocarbons mentioned above at a $C_I$ column pressure of 9 to 10 bars absolute (1 bar=$10^5$ Pa), for example, and which is normally the highest boiling point constituent apart from the MTBE, is present in the distillate and thus in line 10. Because of the overhead refluxing, the MTBE content in the distillate is maintained, for example, below 100 molar ppm.

The distillate, preferably condensed in heat exchanger 43 and containing azeotropic methanol, is introduced at its bubble point into first extractive distillation column $C_{II}$ which has an equivalent of 50 theoretical plates operating at 6.5 bars absolute, at a level located substantially at the column centre. In the upper portion of the column, for example at the level of the 6th theoretical plate, a liquid phase stream of a non aqueous solvent which is selective towards olefin hydrocarbons, for example N,N-dimethylformamide (DMF), is introduced via line 13 at a temperature of about 50° C.

A solvent to feedstock ratio of about 5:1 is advantageously maintained to ensure recovery of at least 92% by weight of the olefins contained in the feedstock in the bottom fraction from the extractive distillation step.

The distillate mainly contains saturated hydrocarbons and generally does not contain more than 5% of olefins.

This distillate is normally condensed at 6 bars absolute using conventional heat exchanger 44 at room temperature. A portion of the condensate is recycled as reflux via line 14 while a further portion is recovered via line 15 either for storage or for transport to an alkylation unit. A portion of the distillate stream (line 16) can also be extracted via line 15 and used as a coolant as will be described below.

The DMF content in the distillate is normally held below 15 ppm by maintaining a reflux to distillate ratio of about 4.0. The lower portion of the first extractive distillation column is brought to the boil using vapour at an appropriate temperature. A portion of the heat required is supplied by heat exchange with the hot solvent in reboiler 17. The bottom fraction from the extractive distillation step containing olefins, methanol and solvent is sent via line 18 at a temperature of 112° C. to the 15th theoretical plate level of a second extractive distillation column $C_{III}$, with an equivalent of 45 theoretical plates. This column is operated at a pressure at which, in the presence of methanol as a co-solvent, the temperature at the bottom of the column preferably does not exceed 160° C. Adjusting the methanol content to a concentration greater than that of the azeotrope means that higher pressures can be used. Under these conditions, the overhead reflux of $C_4$ olefin hydrocarbons can be condensed at a higher temperature close to room temperature. It is thus of advantage to reduce the temperature of the DMF-methanol mixture by introducing fresh methanol via line 4 into the lower portion of column $C_{III}$ and/or introducing methanol via line 34 for example at the same plate as that of line 4 from a stripping stage which is described below.

The operating pressure in column $C_{III}$ is, for example, such that the $C_4$ olefin distillate is completely condensed at a bubble point of about 10° C., equivalent to a pressure of 1.5 bars absolute. If only azeotropic methanol is introduced into column $C_{III}$ with the DMF solvent, the bottom temperature of the column can reach 200° C., for example, at a bottom pressure of 2.0 bars absolute. Thus, in order to limit the temperature to about 160° C., for example, a substantial quantity of fresh methanol must be added as co-solvent to the bottom of the column via line 4.

The ratio of reflux (line 21) to distillate is, for example, kept to a value of 0.30, to ensure that the DMF content in the olefin-rich distillate (line 20) is at most 12 ppm by weight. In the embodiment described above consisting of adding a portion of the methanol-containing effluent (line 34) from the stripping step to the azeotropic methanol, a pressure of 4 bar, for example, can be used in column $C_{III}$ without exceeding a bottom temperature of 160° C. In such a scheme, the distillate can be condensed at temperatures of 30° C. to 40° C.

In order to condense the distillate from the second extractive distillation at 10° C., for example, a portion of the condensed isobutane-rich overhead fraction (line 16) from column $C_{II}$ is used as an internal refrigerant in chiller 22 where it is vaporised in the grill at a pressure which is slightly above atmospheric pressure and at 0° C. Compressor 23 driven by an electric motor compresses the stream of vaporised isobutanes to a pressure which is the same as that in the first extractive distillation column $C_{II}$ and thus allows condensation of this cooling stream in condenser 44. The process of the invention thus only requires one compressor to condense the overhead vapours from the second extractive distillation step.

Line 33 connected to DMF introduction line 27 in column $C_{II}$ can be connected at the level of the 6th theoretical plate of column $C_{III}$. Entrainment of methanol towards the isomerisation reactor is thus avoided.

The extractive distillation residue is pumped (line 24) to stripping column $C_{IV}$ which has an efficiency equivalent to 30 theoretical plates and operates substantially at atmospheric pressure to avoid exceeding the temperature of 160° C., for example, at the bottom of the column.

The feedstock for this column is introduced at the 19th theoretical plate level and is distilled so that methanol is delivered overhead (line 26) which, once condensed, is recycled to synthesis reactor 6 via line 2, and a stripping residue containing DMF solvent which is recycled via line 27 to column $C_{II}$ is delivered after cooling to 50° C.

The solvent can be cooled by removing a portion of a liquid mixture from the last third (boiler side) of the first extractive distillation column $C_{II}$, where the temperature is 10° C. to 40° C. below that at the bottom of the column; a portion of this liquid mixture is then vaporised by heat exchange in heat exchanger 17 using the hot solvent from the recycling step and the partially vaporised liquid mixture is reintroduced at substantially the same point. The recycling solvent can also be cooled by using part of it as the hot fluid in reboiler 46 at the bottom of the column $C_I$. The heaviest compounds and degradation products can be removed from the solvent either continuously or intermittently in regenerator 29 connected to recycle line 27 via line 28 and by exit line 28a connected to the bottom of column $C_{IV}$.

In order to ensure good quality methanol, the overhead from stripping column $C_{IV}$ is refluxed (line 30) at a ratio of 3.0 to 1 with respect to the distillate (line 26).

This reflux allows the DMF content to be reduced to less than 10 ppm, thus avoiding poisoning of the catalyst in the synthesis reactor.

In a further embodiment, if the DMF content in the methanol-containing distillate from the stripping column is too high for direct recycling to the reactor, it can be purified by sending at least a portion of the distillate to depropanizer 31a downstream of skeletal isomerisation unit 5 via line 25 connected to line 26.

The fraction containing DMF then passes into debutanizer 31b and the DMF is recovered from the residue (line 32) which also contains $C_5^+$ by-products. The residue can be mixed with petrol as concentrations of the order of a few parts per million of DMF constitute a good additive for petrol.

At least a portion of the residue can be recycled to distillation column $C_1$ via line 9 connected to line 32.

Finally, a portion of the distillate (line 20) from column $C_{III}$ is introduced after condensation into skeletal isomerisation unit 5, which conventionally comprises an isomerisation reactor connected to depropanizer 31a which is in turn connected to debutanizer 31b. The overhead fraction from the depropanizer (line 60) contains $C_3$ hydrocarbons which are collected. The remaining fraction containing isomerised $C_4$ olefin hydrocarbons, $C_5^+$ hydrocarbons, any methanol present and traces of DMF as indicated above, is introduced into debutanizer 31b via line 61. An overhead fraction containing isomerised $C_4$ olefins and any methanol is condensed, a portion of the condensate being used as reflux while the other portion is recycled via line 2 to MTBE synthesis reactor 6.

It should be noted that the distillates from columns $C_I$, $C_{II}$ and $C_{IV}$ which are recovered in the gaseous phase respectively pass through heat exchangers 43, 44 and 45 to condense them, a portion of the condensate being used as reflux. Similarly, at the bottom of columns $C_I$, $C_{II}$, $C_{III}$ and $C_{IV}$, a portion of the residues obtained is vaporised in heat exchangers 46, 47, 48 and 49 respectively and reintroduced into the columns. These constitute standard reflux arrangements for the skilled person.

The above apparatus would be identical for the etherification of a $C_5$ fraction except that the condensed overhead fraction from column $C_{II}$ could not be used as an internal coolant and the depropanizer and debutanizer would be respectively replaced by a debutanizer to which either a depropanizer or a depentanizer could be connected.

EXAMPLE

A fluidised bed catalytic cracker (FCC) supplied 40180 kg/h of a dry effluent constituted by a $C_4$ fraction whose composition is given in the summary table below.

The conventional MTBE synthesis process using two reactors 6 and 6a converted up to 97% of isobutene contained in the feedstock, which was reacted with 123 kmoles/h of fresh methanol introduced via line 3. A recycling stream 2 or 26 equivalent to the quantity of methanol stripped by azeotropy with the distillate from column $C_1$ was added to the fresh methanol to bring the total quantity of methanol to 154 kmoles/h.

123 kmoles/h of methanol was reacted with the fresh isobutene feedstock to produce 123 kmoles/h of MTBE which was recovered as a residue from distillation column $C_1$ which operated at 11 bars absolute. The distillate (line 10) contained 31 kmoles/h of azeotropic methanol and 580 kmoles/h of $C_4$ cut and unconverted isobutene, giving a methanol content of about 5 mole % in the total distillate. Distillate 10 constituted the feedstock for the first extractive distillation column $C_{II}$ and had a composition which can be deduced from the summary table below.

166 000 kg/h of recycled dimethylformamide (DMF) was introduced into column $C_{II}$ at 50° C. at the 6th theoretical plate level. All the DMF and methanol, about 10% of the $C_4$ saturated hydrocarbons and more than 95% of the $C_4$ olefins were recovered as residue (line 18) at a temperature of 112° C. and a pressure of 7.0 bar absolute.

The distillate collected in line 15 or 16 had the composition shown in the summary table. The residue obtained from line 18 which contained 20 645 kg/h of methanol and $C_4$ olefin hydrocarbons in 166 000 kg/h of DMF, was sent under pressure to second extractive distillation column $C_{III}$ which operated at an overhead pressure of 2.0 bars absolute. 4600 kg/h of DMF was added via line 33 at the 6th theoretical plate level of column $C_{III}$. This column delivered a distillate via line 20 whose composition can be deduced from the table below. This distillate was introduced into the skeletal isomerisation reactor.

The residue from column $C_{III}$ (line 24) was sent to stripping column $C_{IV}$ which had an efficiency equivalent to 30 theoretical plates.

This residue contained methanol as co-solvent at a concentration which can vary from a minimum value corresponding to the azeotropic concentration with the hydrocarbons from column $C_I$ up to a maximum corresponding to that added via lines 4 and 34. In the present example, the methanol content corresponded to the azeotropic composition to which 4000 kg/h of methanol was added.

The feedstock for the stripping column $C_{IV}$ was introduced at the 19th theoretical plate level. The column operated at a pressure just above atmospheric pressure, allowing the methanol to condense by indirect cooling with air at about 45° C. A portion of the condensed methanol was reintroduced as reflux in the ratio of 2.6:1. Under these conditions, less than 10.0 ppm by weight of DMF remained in the methanol. This was recycled with the effluent from the isomerisation reactor to the MTBE synthesis reactor.

The bottom fraction from the stripping column (line 27) contained solvent with 0.002% to 0.5% by weight of methanol and lighter compounds.

The material balance is shown in the following table:

| Constituents | Effluents FCC | Feed $C_{II}$ | Distillate $C_{II}$ | Distillate $C_{III}$ | Methanol* | Distillate $C_{IV}$ |
|---|---|---|---|---|---|---|
| C3 | 22.67 | 22.67 | 22.67 | — | — | — |
| Isobutane | 179.94 | 179.94 | 179.90 | 0.04 | — | — |
| Isobutene | 125.07 | 1.24 | 0.64 | 0.60 | — | — |
| 1-butene | 103.86 | 103.78 | 11.95 | 91.83 | — | — |
| N-butane | 54.28 | 54.28 | 38.27 | 16.01 | — | — |
| 2-trans butene | 120.13 | 120.04 | 0.08 | 120.25 | — | 0.07 |
| 2-cis butene | 96.78 | 96.74 | — | 96.64 | — | 0.10 |
| C5+ | 7.64 | 1.09 | — | 1.00 | — | 0.09 |
| Methanol | — | 31.00 | — | — | 125.0 | 156.0 |
| DME | — | 0.22 | — | 0.10 | — | 0.12 |
| DMF | — | — | — | — | — | — |
| Total (kmoles/h) | 710.37 | 611.0 | 253.51 | 334.28 | 125.0 | 156.38 |
| Molar mass | 56.56 | 55.89 | 56.76 | 56.26 | = | 33.50 |
| kg/h | 40 180 | 34 150 | 14 370 | 18 500 | 4 000 | 5 280 |

*Methanol introduced in second extractive distillation.

What is claimed is:

1. A process for the production of a tertiary ether comprising the following steps:

a) reacting a hydrocarbon feedstock containing saturated hydrocarbons and tertiary iso-olefinic hydrocarbons with an alcohol which is methanol if or methyltertioamylether (TAME), the product is methyltertiobutylether (MTBE)/or ethanol if the product is ethyltertiobutylether (ETBE) or ethyltertioamylether (ETAE), in at least one catalytic reaction zone (6) to produce an effluent containing the tertiary ether, b) distilling the effluent in a distillation zone ($C_I$) under suitable distillation conditions, the tertiary ether being recovered from the bottom of the tertiary ether distillation zone, and a distillate containing olefin hydrocarbons, at least a portion of said alcohol and saturated hydrocarbons which may be at least partially condensed, being recovered overhead, c) carrying out extractive distillation of the distillate from step b) in a first extractive distillation zone ($C_{II}$) under appropriate first extractive distillation conditions, in the presence of a non aqueous solvent which is selective for olefin hydrocarbons, at least a portion of which is introduced into said first zone and an overhead fraction being recovered which is rich in at least a portion of the saturated hydrocarbons which is at least partially condensed, a bottom fraction also being recovered from the first extractive distillation step, d) carrying out extractive distillation of the bottom fraction from step c) in a second extractive distillation zone ($C_{III}$), under suitable second extractive distillation conditions, and recovering overhead at least a portion of a second extractive distillation distillate which is rich in olefin hydrocarbons and which is at least partially condensed, a residue containing mainly alcohol and solvent also being recovered from the bottom, e) separating the residue from step d) in a separation zone ($C_{IV}$), under appropriate separation conditions, and recovering overhead at least a portion of the alcohol and recycling it at least in part to step a), and recovering solvent from the bottom and recycling it at least in part to step c), and f) carrying out skeletal isomerisation of the distillate from step d) in a skeletal isomerisation zone under appropriate skeletal isomerisation conditions, the zone comprising at least one separation zone for the isomerisation effluents, recovering from said separation zone a first isomerisation distillate containing light hydrocarbons from the separation zone and a second isomerisation distillate containing tertiary isoolefin hydrocarbons which is recycled to step a).

2. A process according to claim 1 wherein fresh methanol in the case of MTBE or TAME production or fresh ethanol in the case of ETBE OR ETAE production is introduced into the second extractive distillation zone ($C_{III}$) at a level which is lower than that where the bottom fraction from step c) is introduced, in a ratio of alcohol to bottom fraction of between 0.001 and 1.0.

3. A process according to claim 1 wherein a portion of the alcohol from step e) is recycled to the second extractive distillation zone ($C_{III}$) at substantially the same level as that for the introduction of the bottom fraction from step c), in a ratio of alcohol to bottom fraction of between 0.001 and 1.0.

4. A process according to claim 1 wherein the feedstock is a $C_5$ fraction.

5. A process according to claim 1 wherein the feedstock is a $C_4$ fraction.

6. A process according to claim 5 wherein a portion of the condensed overhead fraction from step c) is vaporised in the grille of a heat exchanger (22) to condense the distillate from the second extractive distillation step.

7. A process according to claim 1 wherein the remaining portion of solvent not introduced at step c) is recycled to the second extractive distillation zone ($C_{III}$) to a plate which is above that of the supply for the bottom fraction from step c).

8. A process according to claim 1 wherein at least a portion of the alcohol recycled to step a) is purified in the separation zone for the effluent from the skeletal isomerisation step.

9. A process according to claim 1 wherein a residue containing $C_5^+$ or $C_6^+$ hydrocarbons is recovered from the bottom of the separation zone for the isomerisation effluents and recycled at least in part to the distillation zone ($C_I$) at a plate which is lower than that for the supply of the effluent from the catalytic reaction zone to zone ($C_I$).

10. A process according to claim 1 wherein the conditions in the extractive distillation zone ($C_{II}$) are as follows:

Total efficiency (in theoretical plates): more than 20,

Pressure: 1 to 25 bar;

Solvent to feedstock ratio: 3 to 10,

Reflux ratio: more than 0.1.

11. A process according to claim 1 wherein the conditions in the second extractive distillation zone ($C_{III}$) are as follows:

Total efficiency (in theoretical plates): more than 10;

Pressure: 1 to 15 bar;

Solvent to feedstock ratio: 0.01 to 0.5 preferably 0.02 to 0.1;

Reflux ratio: more than 0.1.

12. A process according to claim 1 wherein the conditions in the separation zone ($C_{IV}$) are as follows:

Total efficiency (in theoretical plates): more than 5;

Pressure: 0.1 to 3 bar,

Reflux ratio: more than 0.2.

13. A process according to claim 1 wherein a portion of the liquid mixture in the last third of the first extractive distillation column ($C_{II}$), with a temperature 10° C. to 40° C. below that at the bottom of said column, is removed and partially vaporised by heat exchange with the solvent from the separation step and the partially vaporised liquid mixture is reintroduced at substantially the same point.

14. A process according to claim 1 wherein a portion of the tertiary ether is reboiled by indirect heat exchange with a portion of the solvent from the separation step.

15. A process according to claim 1 wherein the solvent is N,N-dimethylformamide, N,N-diethylformamide, N,N-dimethylacetamide, formylmorpholine, N-methylpyrrolidone, butyrolactone or furfural.

16. A process according to claim 1 wherein the residue is recovered from the bottom of the second extractive distillation zone ($C_{III}$) at a temperature of at most 220° C. (step d)).

17. A process according to claim 10, wherein the number of theoretical plates is 40 to 50, the solvent to feedstock ratio is 4 to 6, and the reflux ratio is 1 to 6.

18. A process according to claim 11, wherein the number of theoretical plates is 25 to 35, the solvent to feedstock ratio is 0.02 to 0.1, and the reflux ratio is 0.2 to 1.

19. A process according to claim 12, wherein the number of theoretical plates is 10 to 35, the pressure is 0.6 to 1 bar, and the reflux ratio is 1.5 to 3.5.

20. A process according to claim 1, wherein the solvent is N,N-dimethylformamide.

21. In a process suitable for the production of a tertiary ether, the following steps:
   a) reacting a hydrocarbon feedstock containing saturated hydrocarbons and tertiary iso-olefinic hydrocarbons with an alcohol which is methanol when the product is methyltertiobutylether (MTBE) or methyltertioamylether (TAME), or ethanol when the product is ethyltertiobutylether (ETBE) or ethyltertioamylether (ETAE), in at least one catalytic reaction zone (6) to produce an effluent containing the tertiary ether,
   b) distilling the effluent in a distillation zone ($C_I$) under suitable distillation conditions, the tertiary ether being recovered from the bottom of the tertiary ether distillation zone, and a distillate containing olefinic hydrocarbons, at least a portion of said alcohol and saturated hydrocarbons optionally at least partially condensed, being recovered overhead,
   c) carrying out extractive distillation of the distillate from step b) in a first extractive distillation zone ($C_{II}$) under suitable first extractive distillation conditions, in the presence of a non aqueous solvent selective for olefinic hydrocarbons, at least a portion of said non-aqueous solvent being introduced into said first zone, an at least partially condensed overhead fraction rich in the saturated hydrocarbons being recovered, a bottom fraction also being recovered from the first extractive distillation step, and
   d) carrying out extractive distillation of the bottom fraction from step c) in a second extractive distillation zone ($C_{III}$), under suitable second extractive distillation conditions, and recovering overhead at least a portion of a second extractive distillation distillate rich in olefinic hydrocarbons and which is at least partially condensed, and a residue containing mainly alcohol and solvent being recovered from the bottom of said second extractive distillation zone.

* * * * *